United States Patent
Tranquilla

Patent Number: 5,554,807
Date of Patent: Sep. 10, 1996

[54] BELT DAMPING

[76] Inventor: Michael N. Tranquilla, 16823 Fitzgerald, Livonia, Mich. 48154

[21] Appl. No.: 418,221

[22] Filed: Apr. 6, 1995

[51] Int. Cl.$^6$ ............................................. G01M 19/00
[52] U.S. Cl. .................................. 73/579; 73/11.04
[58] Field of Search .................... 73/18.04, 12.01, 73/12.09, 579, 580, 581, 582, 862.453, 430

[56] References Cited

U.S. PATENT DOCUMENTS 5,269,181  12/1993  Gibson et al. ........................ 73/579
5,410,906  5/1995  Austin et al. ......................... 73/11.04

*Primary Examiner*—Richard Chilcot
*Assistant Examiner*—Ronald Biegel

[57] ABSTRACT

A method of determining damping coefficients for a resilient web, involving: stretching a prescribed length of the web between a pair of pulleys mounted on a frame; attaching a prescribed test mass $M_o$ upon this length at a prescribed distance $L_1$ from one pulley; shaking the frame at resonance frequency $f_R$, while deriving the resonance-amplitude; and using the foregoing to determine web damping coefficients.

21 Claims, 5 Drawing Sheets

TENSION-COMPRESSION
BAR MODEL

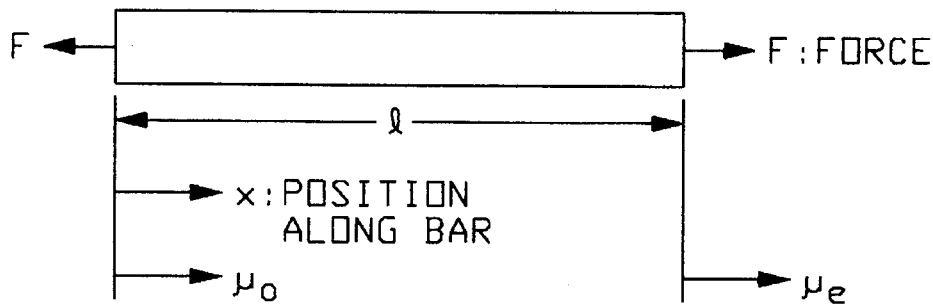

$\mu_o, \mu_e$ : DISPLACEMENTS $\dfrac{d\mu}{dx} = \epsilon$, STRAIN $\mu = \displaystyle\int_0^x \epsilon\, dx + \text{CONSTANT}$

STRESS-STRAIN RELATIONSHIP $\sigma = E\epsilon + q\dfrac{d\epsilon}{dt}$ , $\sigma$ : STRESS
$\phantom{\sigma = E\epsilon + q\dfrac{d\epsilon}{dt}\,,\,}$ $t$ : TIME $E$ : ELASTIC MODULUS $Q$ : DAMPING COEFICIENT $\sigma = \dfrac{F}{A}$ , $A$ : CROSS-SECTIONAL AREA

RESULT:

$\mu_e - \mu_o = \dfrac{F\ell}{AE}\left(1 - e^{-\frac{E}{q}t}\right)$

FIG. 3A

LUMPED PARAMETER MODEL $$F_c = c\left(\frac{d\mu_e}{dt} - \frac{d\mu_e}{dt}\right)$$

$$F_K = k(\mu_e - \mu_o)$$

$$F = F_c \div F_k$$

RESULT:

$$\mu_e - \mu_o = \frac{F}{k}\left(1 - e^{\frac{k}{c}t}\right)$$

COMPARE WITH BAR MODEL $$k = \frac{AE}{\ell}$$

$$c = \frac{Aq}{\ell}$$

BELT DAMPING

This disclosure relates to belts for transmitting motion (e.g., between shafts, with tension transfer and the like), and particularly to techniques for determining damping coefficients therefor.

BACKGROUND, FEATURES

Workers making or using flexible web means (e.g., belts used to transmit motion from one shaft to another) have long been concerned about the complications now typically associated with determining damping characteristics (e.g., damping coefficient) of such a web. Typically, this may involve "trial-and-error" testing of the actual belt in the actual mechanism; or it may require a specific sample size, or it may require that the belt be permanently altered in some way; or "over-stressed" in actual use-environment.

This invention addresses such concerns, and teaches a technique and apparatus for determining such damping coefficients:

without need of trial-error testing of an actual belt length in an actual use-environment, or any associated belt altering or overstressing;

without need of any specific sample size or belt-length (e.g., testing one length can determine damping for many different lengths).

Thus, it is an object hereof to alleviate such problems and provide at least some of the here-described features and advantages. A more particular object is to provide means for quantifying belt damping parameters—especially for various belt-lengths, yet by testing at only a few belt-length positions. Another object is to do so by subjecting the belt to sinusoidal shaking at resonance conditions.

A further object is to avoid conventional solutions, such as testing a belt in the mechanism it is to be used in.

Other objects and advantages of the present invention will be apparent to those skilled in the art.

BRIEF DESCRIPTION OF THE DRAWINGS

The foregoing and other features and advantages of the present invention will be appreciated by workers as they become better understood by reference to the following detailed description of the present preferred embodiments, these being considered in conjunction with the accompanying drawings, wherein like reference symbols denote like elements:

FIGS. 3A, 3B give related analysis.

DETAILED DESCRIPTION

Figure 1:
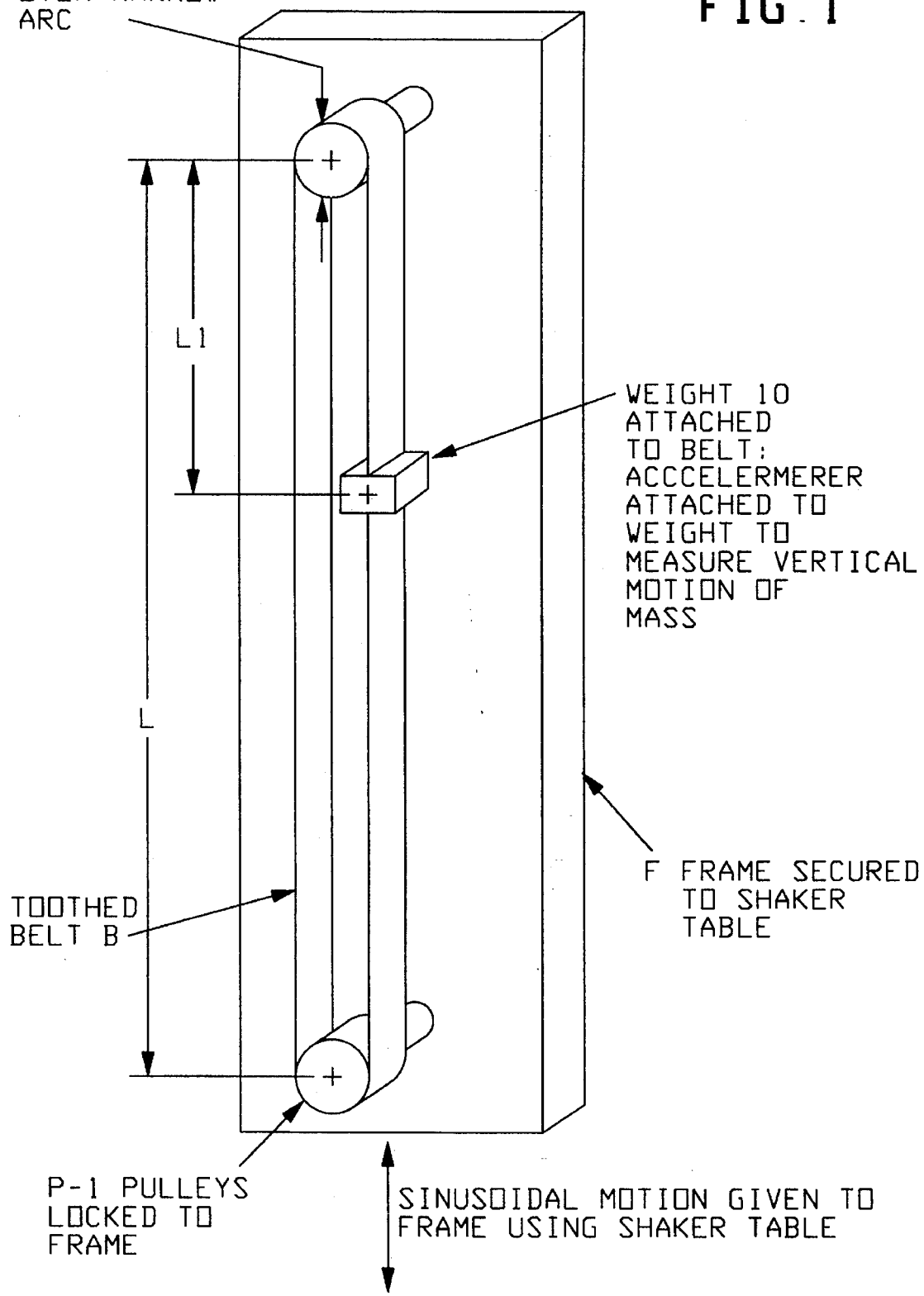
FIG. 1 is a very schematic, idealized showing of a preferred belt tensioning/shaking arrangement.

FIG. 1 shows a frame F which is relatively rigid when compared to the belt B being tested, being secured to a shaker table (not shown) adapted to experience a known sinusoidal motion. Pulleys P-1, P-2 are affixed on the frame F. A length of belt B (endless-loop or not; also includes any belt-like, web material) is stretched over, and between, the pulleys P-1, P-2. The distance L between pulleys is adjustable so that a desired tension may be produced in belt length B. Such tensioning is well known to those practiced in the related arts. Belt B is clamped to the pulleys over a narrow arc, away from the points where the belt segments are tangent to the pulleys. This prevents gross relative motion between the belt and the pulleys.

A weight 10 of known mass (test mass m), is clamped to belt B at some known distance L1 from the center of one pulley P-2. Various known means of clamping may be used, such as a common C-clamp as known in the art. This clamp, with any needed transducer attached to it, should have its center of gravity near the (width, and thickness) axis of belt B.

Motion-Detect means MD is used for measuring the vertical motion-amplitude of mass m, either relative to the shaker table or relative to the same reference as the shaker motion. This may be accomplished by any one of many well known expedients such as: an accelerometer or like transducer (with indicator also used, if desired—see Gig. 2), or a recording pen, or a light beam reflected off the mass m onto a scale, or an electromagnetic voltage generator, etc. For illustration purposes, accelerometers will be preferred here to measure motions of both the mass m and the shaker table. Such accelerometers are well known to artisans familiar with motion transducers. For illustration purposes, these accelerometers are assumed to measure acceleration relative to the earth. Piezo-electric accelerometers are well known examples and preferred. Or, one may equivalently measure velocity or displacement, instead of acceleration, as artisans understand.

The belt and frame assembly is mounted to the shaker table so that the length of the belt L, under test, lies along the same direction as the motion of the shaker table (see arrow FIG. 1). Motion of the shaker table is transmitted to the mass m (along plane of frame F) via pulleys P-1, P-2 and belt B wound thereon.

The motion of mass m may, or may not, have the same amplitude as that of the shaker table because of the longitudinal (i.e.,; tension and compression) flexibility of the belt B. Belt B and object 10 clamped thereon may be viewed as, essentially, the equivalent of a spring and mass system, having a resonant frequency $f_R$. It will be assumed that when a spring and mass system is shaken at its resonant frequency, the motion of the mass is limited only by the damping in the system. Here, belt B is assumed to provide the only significant loss of energy in this system, thus damping must be, essentially, entirely due to the (dynamic) belt stretching. Here, it will be assumed that a damping coefficient, c, in units of force per unit velocity, can be derived by the following equation:

$$c = 4*\text{pi}*m*f_R xs/(xm - xs), \text{ or } 4\pi\, mf_R \frac{xs}{xm - xs},$$

Figure 2:
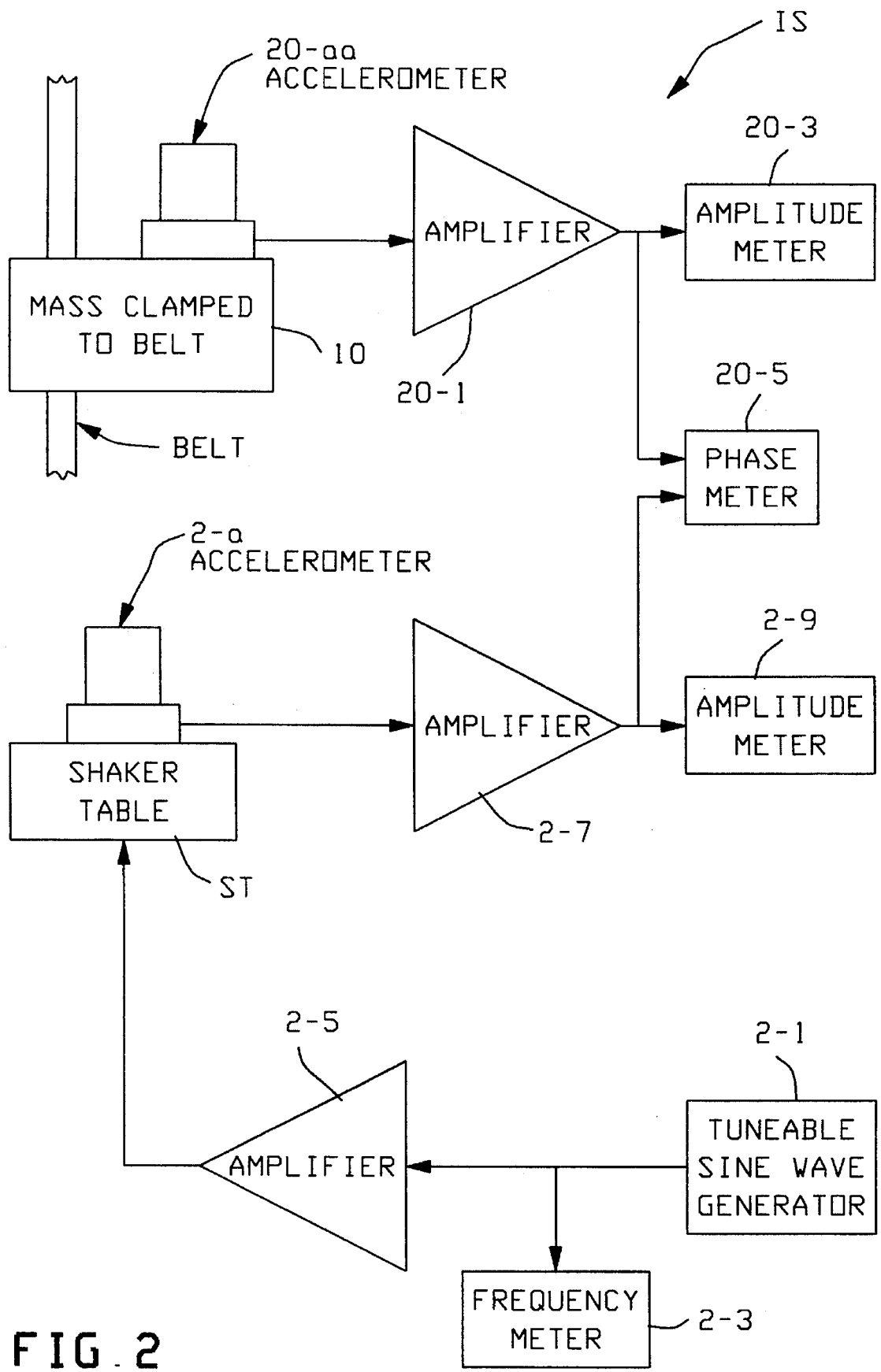
FIG. 2 illustrates a preferred measurement array for measuring belt damping for an arrangement like that of FIG. 1.

Where:

pi=3.14159 m: mass of the object clamped to the belt B $f_R$: frequency of sinusoidal motion at resonance xs: absolute value of motion amplitude for shaker table xm: absolute value of amplitude for motion of mass m, System for measuring damping (FIG. 2):

FIG. 2 is a block diagram of a preferred, related instrumentation system IS for determining belt damping-coefficient C. A tunable sine wave generator 2-1 is used to output a sine wave voltage at a selected frequency, (this may be monitored by associated frequency meter 2-3, and this sine wave voltage from generator 2-1 may be input to an amplifier 2-5). Generator 2-1 is coupled to drive an electrodynamic shaker table st. (This may alternatively be a electro-hydraulically-driven shaker table.) The shaker table motion is preferably detected by an accelerometer 2-a (or like amplitude transducer means) whose electrical output may be fed (e.g., via an amplifier 2-7 if needed), to an amplitude meter 2-9 which may indicate the value xs (shake-amplitude for table st) if desired.

Similarly, an accelerometer 20-aa is attached to the mass m (that is clamped onto the belt, and its output may be fed to an amplifier 20-1, and then to an amplitude meter 20-3 if desired, to indicate the value xm (shake-amplitude for mass m).

In any event, each accelerometer output is fed, in common, to a phase meter 20-5, which measures the relative phase between the peaks of the (sine wave) motions of the mass and table while shaken. The tuneable sinewave generator 2-1 is adjusted until these relative phases are at 90° degrees.

This 90° degree phase relation is here assumed to occur at "resonance". One example for so measuring phase is with the use of Lisajou figures on an oscilloscope. Another way to measure phase, as well as amplitude, is with an FFT analyzer. These devices are in common use. The frequency at which the 90° degree phase relation occurs is, of course, resonant frequency: the value $f_R$ used in the above equation.

Note: the equation above for determining value C has no dependence on belt length. If mass m is clamped at a different position along the belt length, and the measurement process repeated, a different value of c will result. It will be shown that this should occur by reference (below), to FIG. 3, and will use this as a straight-forward "stress-strain, tension/compression bar model" to derive force-displacement equations in terms of elastic and damping parameters. When compared with the force-displacement equation for the "lumped parameter" model, FIG. 4, it will be seen that any segment of such a belt should have a damping coefficient which is inversely proportional to belt length (i.e., $c \sim 1/L$).

Figure 3:
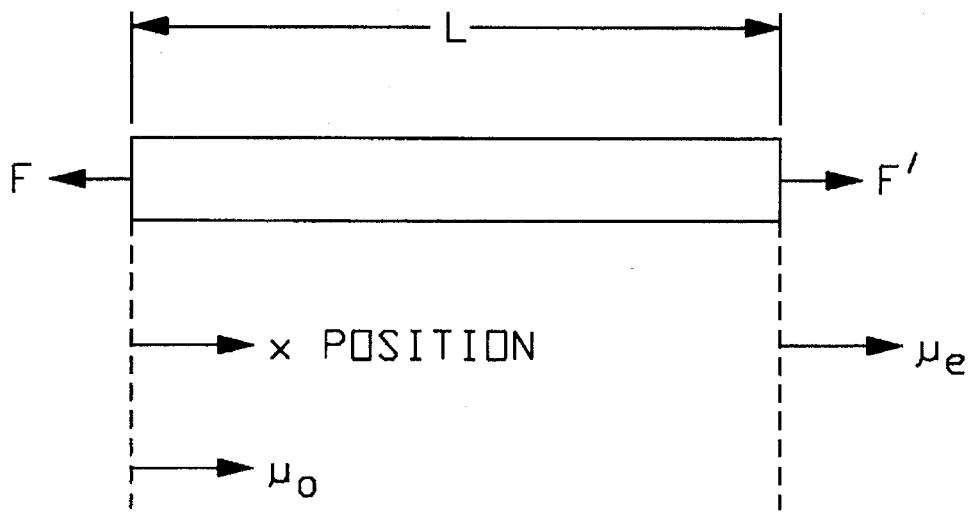
FIGS. 3 and 4 illustrate two models for related analysis.

Analysis per Tension-Compression BAR Model (FIG. 3):

FIG. 3 may be understood as a "BAR model" for analyzing forces F,F' stressing a subject length of such a belt B in tension or compression. The segment will be assumed to have a length L with a test mass m disposed therealong at varied positions x, and the resultant displacements (under sinusoidal shaking at resonance) will be $U_o$, $U_e$ at respective ends.

Assuming that strain $\epsilon$ is defined as du/dx, a displacement U may be defined as the integral;

$$U = \int_0^x \epsilon dx + \text{a constant}$$

Stress $\sigma$ is given as: $\sigma = E \epsilon + q dE/dt$, or $\sigma = F/A$
Where
 $\epsilon$=elastic modulus,
 q=damping coefficient for bar
 t=time
 A=cross-sectional area
Thus, one may represent differential motion, $U_L - U_0$ as:

$$\frac{FL}{AE}(1 - e^{-Et/g})$$

above analysis summarized in FIG. 3a.

Workers will here understand that a belt is really a tension-compression bar model. The Test Fixture, here mentioned, yields data for a "Lumped Parameter" model (e.g., see below, and FIG. 4). The following analysis of the Lumped Parameter model shows how the measured damping data can be related to the "BAR" model.

Figure 4:
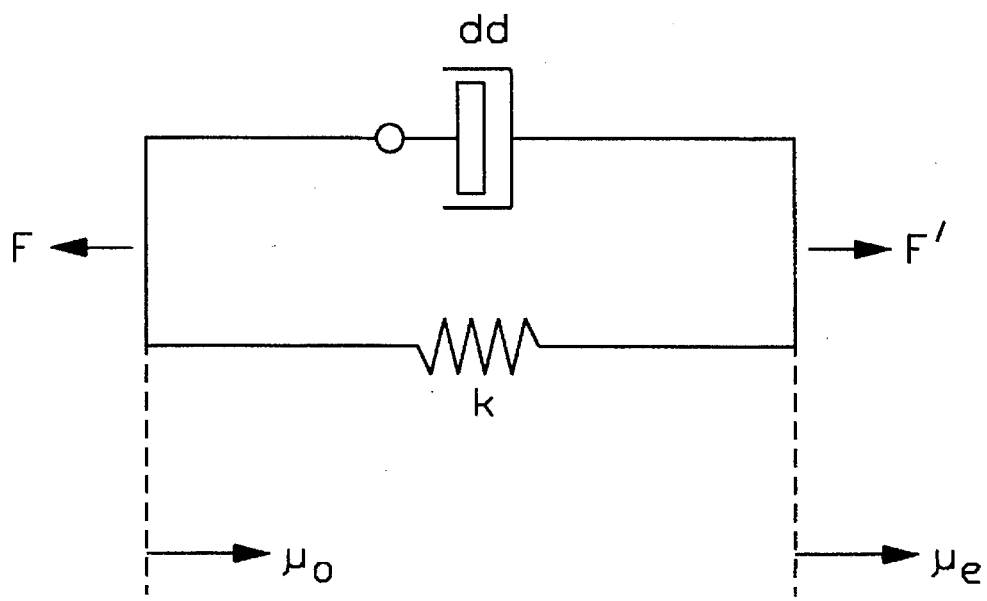
Figure 3B:
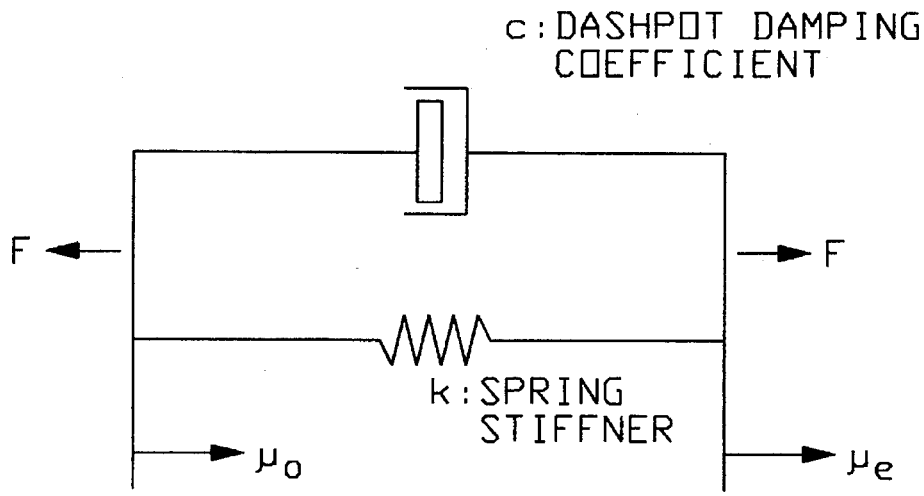

Analysis Via "Lumped-Parameter" model (FIG. 4):

FIG. 4 may be understood as a "Lumped-Parameter" model, to be compared with the BAR model above, Here, cc represents a "dashpot damping coefficient, and K: spring stiffness, with $U_o, U_e$ as before.

At dashpot dd, the damping force $F_{cc}$ may be expressed as:

$$F_{cc} = cc \left[ \frac{du_e}{dt} - \frac{du_o}{dt} \right]$$

At "spring" k, related force $F_k$ may be expressed as:

$$F_k = K(u_e - u_o)$$

Total force F is $F_{cc} + F_k$
Hence, the differential displacement $u_e - u_o$ is:

$$u_e - u_o = F/k (i - e^{KT/c})$$

Comparing with the BAR model:
k=$AE_{/L}$
c=$Aq_{:/L}$
Thus, damping coefficient C is inversely proportional to L, the length of belt being stretched ($c \sim 1/L$).

Since the belt in FIG. 1 has two segments, L1 and L–L1, which are undergoing tension/compression, the related damping coefficient c measured is actually the sum of the two different damping coefficients: $C_2/L_1$ and $C_2/L-L_1$, where $C_2 = A_q$. Additionally, there may be damping at the interfaces where the belt is tangent to the pulleys. This is particularly true for toothed synchronous belts where a belt tooth may rub on a pulley groove during this test. This damping is a constant, since it is not dependent on the position of the clamped mass. The measured damping coefficient c can be described as follows:

$$c = 2*c1 + c2/L1 + c2/(L-L1);$$

or, $$c = 2c_1 + c2/L_1 + c2/L - L_1$$

To obtain the damping coefficients c1 and c2, tests are run for several positions (several L1 values). If only two positions are used, then one can employ a process for solving two linear equations and two unknowns, and so calculate the constants c1 and c2. If more than two positions are used, then one of several well known "least squares, curve fitting" processes can be used to find the "best" values for c1 and c2. An example of such a process is the Marquardt-Levenbert algorithm. of course, using more test positions gives more accurate values for $c_1$ and $c_2$.

This invention will be thus understood to measure damping parameters for resilient belts such that a lumped parameter damping coefficient can be easily calculated for any length of belt (used to transmit motion from one shaft to another).

This is done, principally to determine belt damping coefficients, and so enable an accurate prediction of a belt's dynamic motion performance,—for mechanisms utilizing such belts, so that different belts can be compared for their inherent damping capability, and so that a belt can be "sized" to obtain desirable damping properties.

A salient advantage is that belt damping can be determined without actually testing the belt in the mechanism for using it. Also, one can predict damping for belts of different lengths just by testing one length of belt. A simple test fixture can be used for many different kinds and lengths of belt construction. One can also so test other resilient "belt-like" web materials, such as lengths of: photographic film, magnetic tape, ink ribbon, rope, cables, paper strips, fabric strips, etc.

Advantages Over Past Practice:
— Does not require "trial-and-error" testing in the actual mechanism; and just one belt-length is needed to determine damping for many different lengths;
— Does not require a specific sample size, as virtually any length belt may be used.
— Does not require that the belt be permanently altered in any way; or "over-stressed" or tested in actual use-environment.

Related products for using such belts or belt-like materials are: microfilm film advance mechanisms, document transports, document positioning systems, paper advance mechanisms in printers, pen plotters, magnetic and optical digital storage devices, magnetic tape recorders, printhead positioning mechanisms in typewriters and computer printers, printer ribbon advance mechanisms, optical mirror positioning mechanisms, robots, automatic assembly mechanisms, automotive alternator drives, camshaft drives, and air conditioning compressor drives, automatic adhesive tape dispensers. Such can also benefit from this invention.

In summary, the damping coefficient of a resilient web length is determined by:

1—stretching the length between a pair of pulley means, separated by distance L, and mounted on a relatively fixed frame; with a prescribed test mass m clamped thereon at distance $L_1$ from a pulley;

2—mounting the frame on a shaker table and providing a shaking means (pref. sinusoidal) to shake the frame and test mass while monitoring/adjusting the frequency thereof to arrive at resonance;

3—deriving accelerometer output (amplitude) from this table as it is shaken, while measuring this amplitude $A_T$ at resonance;

4—deriving accelerometer output (amplitude $A_m$) from this test mass m, while measuring this amplitude $A_m$ at resonance;

5—adjusting the generator to shake the table and the mass at resonant frequency $f_R$;
[e.g., doing so via phase monitor, imposing orthogonal phase-relation]

6—computing damping constant $C_1$ and $C_2$ from measurements at two or more mass positions (e.g., $L_1$);

7—and so determining a damping coefficient C according to the relation;

$$C = 2C_1 + C_2/L_1 + C_2/L - L_1, \text{ etc.}$$

Of course, many modifications to the preferred embodiment described are possible without departing from the spirit of the present invention. The invention is not limited to the particular types of sensors or shakers or mountings. Additionally, some features of the present invention can be used to advantage without the corresponding use of other features.

Accordingly, the description of the preferred embodiment should be to be considered as including all possible modifications and variations coming within the scope of the invention as defined by the appended claims.

What is claimed is:

1. A method of determining damping coefficients for a resilient web, comprising:
   stretching a prescribed length of said web between a pair of pulley means mounted on frame means; attaching a prescribed test mass $M_o$ on said length at a prescribed distance $L_1$ from one said pulley means; shaking said frame means at resonance frequency $f_R$, while deriving resonance-amplitude; and using the foregoing to determine damping coefficients.

2. The method of claim 1, wherein said distance $L_1$ is varied N times, with a damping coefficient determined for each distance $L_1$, and these coefficients reconciled.

3. The method of claim 2, wherein said frame is affixed on shake-surface means, and controllable shaking means is applied to so shake said frame means and surface means at resonance frequency.

4. The method of claim 3, wherein said shake means is controlled to execute sinusoidal shake vibration.

5. The method of claim 4, wherein the resonant amplitudes of said surface means and said test mass $M_o$ are derived.

6. The method of claim 5, wherein accelerometer and transducers are used to indicate said amplitudes.

7. The method of claim 6, wherein phase is monitored to determine resonance.

8. The method of claim 7, wherein N different mass-distances $L_1$ are selected and damping coefficient determined for each, with an overall damping coefficient for the belt derived therefrom.

9. The method of claim 1, wherein said web comprises a belt for transmitting motion.

10. The method of claim 9, wherein shaking is performed by tuneable sine-wave generator means.

11. The method of claim 8, wherein a damping coefficient C is derived according to the relation:

$$c = 4\pi \, mf_R \frac{xs}{xm - xs},$$

Where:
pi=3.14159
m: mass of the object clamped to the belt B
$f_R$: frequency of sinusoidal motion at resonance
xs: absolute value of motion amplitude for shaker table
xm: absolute value of amplitude for motion of mass m.

12. An arrangement for determining damping coefficients for a resilient web, comprising:
   frame means with pulley means for stretching a prescribed length of said web there-between; said pulley means mounted on said frame means; a prescribed test mass $M_o$ mounted on said length at a prescribed distance $L_1$ from one said pulley means; shake means for shaking said frame means at resonance frequency $f_R$, sensor means for deriving the resonance-amplitude of said mass and said frame means, with the foregoing being used to determine damping coefficients for each distance $L_1$.

13. The arrangement of claim 12, where said distances $L_1$ are varied and a damping coefficient determined at each distance.

14. The arrangement of claim 13, where said frame is affixed on shake-surface means, and controllable shaking means is applied to so shake said frame means and surface means, plus said mass.

15. The arrangement of claim 14, where said shaking means is arranged to execute sinusoidal vibration.

16. The arrangement of claim 15, where shake-transducers are coupled to said mass and said frame/surface means to indicate the resonance said amplitudes.

17. The arrangement of claim 16, where phase detect means is used to determine resonance.

18. The arrangement of claim 17, where said web comprises a belt for transmitting motion.

19. The arrangement of claim 18, where tuneable sine-wave generator means is used for said shaking.

20. The arrangement of claim 19, where a damping coefficient C is derived according to the relation:

$$c = 4\pi\, mf_R \frac{xs}{xm - xs},$$

Where:

pi=3.14159 m: mass of the object clamped to the belt B $f_R$: frequency of sinusoidal motion at resonance xs: absolute value of motion amplitude for shaker table xm: absolute value of amplitude for motion of mass m.

21. The arrangement of claim 15, wherein transducer means are affixed to said test mass and said frame means/surface means, with the outputs thereof are fed in common, to phase detect means whereby to indicate shake-amplitude at resonance.

\* \* \* \* \*